United States Patent [19]

Horiguchi et al.

[11] Patent Number: 5,466,856

[45] Date of Patent: Nov. 14, 1995

[54] METHOD OF PRODUCING CARBONIC DIESTERS

[75] Inventors: Akira Horiguchi, Otake; Shingo Oda, Himeji, both of Japan

[73] Assignee: Daicel Chemical Industries, Ltd., Osaka, Japan

[21] Appl. No.: 283,907

[22] Filed: Aug. 3, 1994

Related U.S. Application Data

[63] Continuation of Ser. No. 112,144, Aug. 26, 1993, abandoned.

[30] Foreign Application Priority Data

Aug. 26, 1992 [JP] Japan .................................. 4-252161

[51] Int. Cl.$^6$ .................................................. C07C 69/96
[52] U.S. Cl. .......................... 558/277; 558/570; 558/274; 558/275
[58] Field of Search ............................... 558/277

[56] References Cited

U.S. PATENT DOCUMENTS 4,625,044  11/1983  Curnutt ................................. 558/270

FOREIGN PATENT DOCUMENTS

| 0429675 | 12/1990 | European Pat. Off. . |
| 568020 | 2/1981 | Japan . |
| 618816 | 3/1986 | Japan . |
| 6143338 | 9/1986 | Japan . |
| WO8707601 | 12/1987 | WIPO . |

Primary Examiner—José G. Dees
Assistant Examiner—Dwayne C. Jones
Attorney, Agent, or Firm—Cushman Darby & Cushman

[57] ABSTRACT

An alcohol, e.g. methanol, carbon monoxide and oxygen are allowed to react in a gas phase in the presence of a solid catalyst comprising a catalyst component, for instance, containing halogen and copper atoms supported on a solid support. The alcohol and carbon monoxide contents of the reactor feed gas are controlled at 1 to 20 volume % and 70 to 95 volume %, respectively. Because the alcohol and carbon monoxide contents of the feed reactant gas are thus controlled, side reactions are considerably inhibited and the object carbonic diester is produced with high selectivity.

24 Claims, No Drawings

METHOD OF PRODUCING CARBONIC DIESTERS

This is a continuation of application Ser. No. 08/112,144, filed on Aug. 26, 1993, which was abandoned upon the filing hereof.

FIELD OF THE INVENTION

The present invention relates to a method of producing a carbonic diester which comprises allowing the corresponding alcohol to react with carbon monoxide and oxygen in the presence of a solid catalyst.

BACKGROUND OF THE INVENTION

Carbonic diesters are compounds of value as automotive gas additives and organic solvents or as reactants, replacing phosgene, in the production of various carbonates, carbamates, urethanes and fine chemicals such as drugs and agrochemicals.

For the commercial production of a carbonic diester, generally the corresponding alcohol is allowed to react with phosgene. However, this known technology demands the use of phosgene having a great toxic potential and, moreover, the reaction of the alcohol with phosgene gives rise to a large quantity of hydrochloric acid which is a highly corrosive substance.

Therefore, a technology has been proposed for producing a carbonic diester without the use of phosgene which comprises allowing the corresponding alcohol to react with carbon monoxide and oxygen in a liquid phase in the presence of a catalyst. The catalyst used for this purpose can be classified into two major categories, i.e. the palladium catalyst including a compound of palladium as the main catalyst component and the copper catalyst including a compound of copper as the main catalyst component.

The reaction using the palladium catalyst is described in Japanese Patent Publication Nos. 8816/1986 and 43338/1986. According to this technology, a palladium compound as the main catalyst component is used in combination with a copper compound and an alkali metal compound. Palladium compounds are advantageous in that they are so active that the reaction proceeds even at a low carbon monoxide partial pressure but has the drawback of giving rise to oxalic acid as a by-product.

The reaction conducted in the presence of a copper catalyst is described in Japanese Patent Publication No. 8020/1981. Copper catalysts are simple in composition and do not give rise to the by-product oxalic acid but since they are less active than palladium catalysts, these catalysts must be used in a large quantity and, moreover, the reaction must be conducted at a high carbon monoxide partial pressure.

However, since the reaction system containing such a catalyst, irrespective of whether it is a palladium catalyst or a copper catalyst, is highly corrosive, the reaction must be conducted in a pressure-resistant reactor having an anticorrosive lining made of e.g. glass or a baked-on type enamel. However, since there is an upper limit to the size of a pressure-resistant reactor having such an anticorrosive lining that can be fabricated, it is difficult to produce a carbonic diester in a liquid phase containing such a catalyst on a commercial scale.

To obviate this corrosion problem associated with a liquid-phase reaction, a technology has been proposed for producing a carbonic diester which comprises allowing the corresponding alcohol to react with carbon monoxide and oxygen in a gas phase in the presence of a solid catalyst. For example, WO87/07601 discloses a production process which comprises allowing all the reactants to react in a gas phase using a catalyst comprising a metal halide supported on a solid support by an impregnation technique. This production process involves a low risk of corrosion and appears to be suited for mass production.

However, as far as the production of dimethyl carbonate starting with methanol is concerned, whereas the liquid-phase reaction provides for a methanol-based selectivity of more than 95% for dimethyl carbonate, the above gas-phase reaction provides only for a low selectivity. Thus, it is disclosed in Example 1 of the above publication that when a feed gas composed of 64.9% carbon monoxide, 10.8% oxygen and 24.3% methanol was introduced through a cupric chloride-on-carbon catalyst bed at a temperature of 115° C. and a pressure of 20 atm, the objective compound was obtained with a selectivity of 80% based on methanol.

Furthermore, WO90/15791 discloses a production process which comprises allowing an alcohol to react with carbon monoxide and oxygen in a gas phase in the presence of a catalyst comprising a copper-tertiary organophosphorus complex supported on activated carbon. In the Examples of this patent literature, the reaction was invariably conducted by feeding a reactant gas mixture of 48.6% carbon monoxide, 2.8% oxygen and 48.6% methanol and the reaction was conducted at a temperature of 150° C. and either at atmospheric pressure or at 6.8 atm. However, according to the check experiments performed by the inventors of the present invention, the selectivities based on methanol under these conditions were in the range of about 80 to 85%.

In these technologies for producing a carbonic diester by gas-phase reaction, the selectivity of the reaction for the objective diester is low and this means not only an increased material cost, viz. the cost of alcohol, but also the need for separation of by-products and these drawbacks add up to a considerable disadvantage in the mass production of a carbonic diester.

SUMMARY OF THE INVENTION

Therefore, the object of the present invention is to provide a method of producing a carbonic diester which involves a minimal risk of corrosion, is conducive to high production, and is capable of providing for a high selectivity for the carbonic diester despite its being a gas-phase reaction.

The inventors of the present invention found, after an energetic research endeavor to accomplish the above-mentioned object, that when the composition of a reactor feed gas is controlled within certain ranges for alcohol and carbon monoxide and the reaction is conducted in a gas phase, the desired carbonic diester can be produced with a very high selectivity, with side reactions being remarkably inhibited and without sacrificing the reaction rate. The present invention has been brought into being on the basis of the above finding.

Thus, the present invention provides a method of producing a carbonic diester which comprises allowing an alcohol to react with carbon monoxide and oxygen in a gas phase in the presence of a solid catalyst using a reactor feed gas controlled at an alcohol content of 1 to 20% by volume and a carbon monoxide content of 70 to 95% by volume.

An alcohol having 1 to 6 carbon atoms such as methanol can be used as the alcohol.

The solid catalyst may contain copper atom. As the solid catalyst containing copper atom, there may be mentioned copper halide such as cuprous halide, copper borate, copper carboxylates such as copper acetate, and so on. The solid catalyst may be a catalyst wherein a catalytically active substance is supported on a solid support such as activated carbon.

The molar ratio of carbon monoxide to alcohol (CO/alcohol) of the feed gas may, for example, range from 3.5 to 95. The molar ratio of carbon monoxide to oxygen (CO/$O_2$) of the feed gas may, for example, range 10 to 200. The molar ratio of alcohol to oxygen (alcohol/$O_2$) of the feed gas may, for example, be about 0.05 to 20.

DETAILED DESCRIPTION OF THE INVENTION

The alcohol mentioned above includes a variety of compounds having one or more hydroxyl groups within the molecule, e.g. saturated aliphatic alcohols such as methanol, ethanol, 1-propanol, 2-propanol and 1-butanol; unsaturated aliphatic alcohols such as allyl alcohol; alicyclic alcohols such as cyclohexanol; aromatic alcohols such as benzyl alcohol and phenol; and polyhydric alcohols such as ethylene glycol and polyethylene glycol. The aromatic alcohol include phenols containing a phenolic hydroxyl group.

The preferred alcohol is a saturated or unsaturated monohydric alcohol, such as alcohols of about 1 to 6 carbon atoms. The particularly preferred alcohol includes methanol and ethanol, with methanol being the alcohol of choice.

The solid catalyst mentioned above may be virtually any solid catalyst for oxidative carbonylation, thus including the halides and salts of transition metals such as copper. From the standpoints of catalytic activity, selectivity of reaction and catalyst life, a solid catalyst containing copper atom is preferred.

The solid catalyst containing copper atom includes copper-containing inorganic, organic and complex compounds. The inorganic compound containing copper atom includes cuprous halides such as cuprous fluoride, cuprous chloride, cuprous bromide and cuprous iodide; cupric halides such as cupric fluoride, cupric chloride and cupric bromide; copper carbonyl halides such as copper carbonyl chloride; copper nitrate; copper sulfate; copper carbonate; copper phosphate; copper borate; and so on. The organic compound containing copper atom includes copper alkoxy halides such as copper methoxy chloride, copper methoxy bromide and copper ethoxy chloride; copper alkoxycarbonyl halides such as copper methoxycarbonyl chloride; copper carboxylates such as copper formate, copper acetate, copper pivalate and copper benzoate; and salts of copper with phenols, such as copper phenoxide. The complex compound containing copper atom includes complexes each formed between an inorganic or organic copper compound such as cuprous chloride or copper acetate and a ligand compound, for example an amine such as ethylenediamine, a nitrogen-containing heterocyclic compound such as pyridine, an organophosphorus compound such as triphenylphosphine or a nitrile such as benzonitrile. The valency of copper may be monovalent or divalent.

Among solid catalysts containing copper atom, solid catalysts containing both halogen and copper atoms are preferred. The halogen atom includes fluorine, chlorine, bromine and iodine.

Among solid catalysts containing both halogen and copper atoms are the above-mentioned cuprous halides, cupric halides, copper alkoxy halides, copper carbonyl halides and copper alkoxycarbonyl halides. Among them, copper halides such as cuprous halides, e.g. cuprous chloride, and cupric halides, e.g. cupric chloride, are particularly preferred.

As the solid catalyst containing both halogen and copper atoms, a solid catalyst consisting of a halogen-containing compound and a copper-containing compound in combination can also be used.

The halogen-containing compound mentioned above includes halides of transition metals such as iron, nickel and cobalt; alkoxy halides (e.g. methoxy chloride) of said transition metals; halides of alkali metals such as lithium, sodium and potassium; and halides of alkaline earth metals such as magnesium, calcium, strontium and barium.

The copper-containing compound mentioned above includes the above-mentioned copper-containing inorganic, organic and complex compounds.

The above-mentioned solid catalysts containing copper atom can be used independently or in combination and even together with a catalyst not containing copper atom, such as compounds of transition metals other than copper, alkali metal compounds and alkaline earth metal compounds.

The solid catalyst for use in the present invention may be a catalyst comprising a catalytically active substance supported on a solid support such as activated carbon, alumina, silica, silica-alumina, titania, zirconia, magnesia, silicon carbide, diatomaceous earth, pumice, alundum or the like by the impregnation, coating, adsorption or other technique or a catalyst prepared by molding a catalytically active substance together with an appropriate binder in the manner of compression molding, extrusion molding or the like.

When use is made of a solid catalyst comprising a catalytically active substance immobilized on a solid support, the proportion of the active substance is generally about 0.1 to 50% by weight and preferably about 0.5 to 20% by weight based on the weight of the support, although the proportion may vary with different species of active substance and support. When a molded catalyst is employed, the proportion of the catalytically active substance is generally about 5 to 99% by weight.

It is an outstanding characteristic of the present invention that the reactor feed gas is controlled at an alcohol content of 1 to 20% by volume and a carbon monoxide content of 70 to 95% by volume.

It should be understood that the terms 'alcohol content' and 'carbon monoxide content' as used in this specification mean the volume percentages of the respective reactants relative to the total amount of three reactants, namely alcohol, carbon monoxide and oxygen, in the reactor feed gas.

When the alcohol content is less than 1% by volume, the reaction rate is not acceptably high. Conversely when the alcohol content exceeds 20% by volume, the proportion of by-products such as formic ester, e.g. methyl formate, and ketal, e.g. methylal, is increased so that the objective carbonic diester cannot be obtained with high selectivity.

On the other hand, when the carbon monoxide content is less than 70% by volume, the proportion of said by-products is increased. When the CO content exceeds 95% by volume, the oxygen content is proportionally decreased so that the reaction rate is adversely affected.

The preferred alcohol content is about 4 to 18% by volume and the preferred carbon monoxide content is about 75 to 95% by volume.

The oxygen content of the reactor feed gas, which represents the balance after deduction of the alcohol and carbon monoxide contents, is generally about 0.5 to 28% by volume and preferably about 1 to 15% by volume.

The carbon monoxide-oxygen feed ratio [$CO/O_2$ (molar ratio)] may for example be about 10 to 200, preferably about 15 to 150, and for still better results, about 20 to 100.

The alcohol-oxygen feed ratio [alcohol/$O_2$ (molar ratio)] may for example be about 0.05 to 20 and preferably about 0.1 to 10. The carbon monoxide-alcohol feed ratio [CO/alcohol (molar ratio)] is generally about 3.5 to 95, preferably about 4 to 40, more preferably about 10 to 40, and for still better results, about 12 to 30.

The selectivity for carbonic diester based on the alcohol is remarkably improved when the carbon monoxide-oxygen feed ratio [$CO/O_2$ (molar ratio)] is controlled within the range of about 10 to 200, preferably about 15 to 150, and more preferably about 20 to 100 and the carbon monoxide-alcohol feed ratio [CO/alcohol (molar ratio)] within the range of about 3.5 to 95, preferably about 4 to 40 and more preferably about 12 to 30.

The feed gas may be a ternary mixture of alcohol, carbon monoxide and oxygen but if necessary such a mixture may be diluted with an inert gas indifferent to the reaction, such as nitrogen, helium, argon and carbon dioxide. In this connection, air may be substituted for oxygen so that nitrogen in the air may be utilized as the diluent gas. It may also be so arranged that the reaction by-product carbon dioxide is recycled to the reaction system for use as said diluent gas.

When the alcohol and carbon monoxide contents of the reactor feed gas are controlled within the respective ranges mentioned above, the selectivity for carbonic diester is remarkably improved without detracting from the reaction rate and with the formation of by-products being remarkably inhibited.

These remarkable effects emanating from the above constitution of the invention may be attributed to the following circumstances.

There is a detailed report on the so-called oxidative carbonylation reaction in which an alcohol, carbon monoxide and oxygen are reacted in a liquid phase in the presence of a copper catalyst to give a carbonic digester, taking dimethyl carbonate as an example [U. Romano et al., Ind. Eng. Chem., 19, 396 (1980)]. According to this report, the mechanism of reaction in the presence of a cuprous chloride catalyst is postulated as follows. (1) In the first place, the cuprous chloride reacts with methanol and oxygen to give copper methoxy chloride, (2) concurrently the cuprous chloride reacts with carbon monoxide to give copper carbonyl chloride, and (3) said copper methoxy chloride interacts with said copper carbonyl chloride to give copper methoxycarbonyl chloride. Then, (4) this copper methoxycarbonyl chloride reacts with the copper methoxy chloride to give rise to dimethyl carbonate and, at the same time, cuprous chloride is regenerated. The above report further states that to insure the stability of copper carbonyl chloride, a carbon monoxide partial pressure must not be less than 20 atm assuming a reaction temperature of, for example, 100° C. In fact, the experimental research undertaken by the inventors of the present invention revealed that in the liquid-phase reaction conducted at a reaction temperature of not less than 100° C., the reaction velocity is considerably lowered when the carbon monoxide partial pressure is less than 10 atm.

On the other hand, the gas-phase reaction involving methanol, carbon monoxide and oxygen in the presence of a solid catalyst is dissimilar to the liquid-phase reaction in that a sufficiently high reaction rate can be realized even at a carbon monoxide partial pressure of less than 10 atm and that methyl formate and methylal as by-products are formed in substantial amounts. However, the detailed reaction analysis made by the inventors of the present invention revealed that although some difference exists between the gas-phase reaction and the liquid-phase reaction in regard to the efficiency of contact between the feed gas and the catalyst and the equillibrium constant of carbonyl complex-forming reaction, the two reactions are roughly identical in terms of the mechanism of reaction and the behavior of active reactant species.

It is, therefore, likely that in the gas-phase reaction, too, dimethyl carbonate is produced in accordance with the reaction mechanism proposed in the above report. Moreover, methyl formate and methylal as by-products are apparently formed as the methyl hydrogen of copper methoxy chloride, which is the product of reaction of cuprous chloride with methanol and oxygen, undergoes β-elimination to yield a formyl group. The β-elimination reaction of copper methoxy chloride and the reaction synthesizing copper methoxycarbonyl chloride, a precursor of dimethyl carbonate, from copper methoxy chloride and copper carbonyl chloride are competive reactions. Therefore, in order to reduce the formation of said by-products, it seems instrumental to generate a large amount of copper carbonyl chloride in the vicinity of copper methoxy chloride on the catalyst surface. For this purpose, we may contemplate an approach comprising reducing the oxygen content of the reactor feed gas or an approach comprising reducing the alcohol content of the feed gas.

According to the method of the present invention wherein a feed gas lean in alcohol, e.g. methanol, and rich in carbon monoxide, is employed, when the reaction is conducted in the presence of a solid catalyst comprising a supported cuprous chloride, a high concentration of copper carbonyl chloride becomes available on the catalyst surface, while the concentration of copper alkoxy chloride, e.g. copper methoxy chloride, is reduced. This results in the presence of a large amount of copper carbonyl chloride in the vicinity of copper alkoxy chloride so that the reaction of copper alkoxy chloride with copper carbonyl chloride occurs in preference to the β-elimination reaction of copper methoxy chloride, with the result that the formation of by-products is remarkably inhibited, thus contributing a great deal to the selectivity of the reaction for the objective dimethyl carbonate. The above hypothesis also suggests that, of the above-mentioned two approaches, the approach toward reducing the alcohol content of the feed gas is more effective.

The method of the present invention can be carried into practice using a fixed-bed reactor or a fluidizedbed reactor. The reaction takes place in a gas phase. The reaction pressure is not so critical but in order to insure a sufficiently high reaction velocity and from the consideration of equipment cost and other economic factors, the reaction is carried out generally at 1 to about 60 atm and preferably at 1 to about 30 atm.

The reaction temperature can be selected from the range wherein the reaction rate is not sacrificed and side reactions are controlled. Thus, for example, the reaction can be conducted at about 20° to 200° C. and preferably about 80° to 150° C. The space velocity of the feed gas flow to the reactor may for example be about 10 to 50000 $h^{-1}$ and preferably about 100 to 5000 $h^{-1}$.

In accordance with the method of the invention wherein the reaction is conducted in a gas phase using a feed gas containing alcohol and carbon monoxide in defined ranges, the corrosion of the equipment is minimized to enable a mass production run and side reactions are considerably inhibited so that dimethyl carbonate can be produced with a remarkably improved selectivity without reducing the reaction rate.

The following examples are intended to describe the present invention in further detail and should by no means be interpreted as defining the scope of the invention.

EXAMPLES

Example 1

Using acetonitrile as the solvent, 3.9 g of cuprous chloride was supported on 50 g of activated carbon (Granular Shirasagi $C_2X$ 4/6-2, specific surface area 1200 m$^2$/g, approx.; Takeda Chemical Industries, Ltd.) in the conventional manner to prepare a solid catalyst.

This solid catalyst was packed into a stainless steel tubular reactor, 10 mm in inside diameter and 450 mm long, to provide a 70 mm-deep catalyst bed. With the reaction temperature being set at 120° C., a mixed gas of CO/O$_2$/methanol=80/4/16 (by volume) was introduced at a space velocity of 500 h$^{-1}$ for 2 hours. During this time, the internal pressure of the tubular reactor was held at 7 Kg/cm$^2$ gauge. The reaction product gas emerging from the outlet of the reactor was condensed by cooling at −70° C. The resulting condensate and the non-condensible gas were respectively analyzed by gas chromatography using the internal standard method and the absolute calibration method.

As a result, dimethyl carbonate was obtained at the rate of 1.0 mole/H per liter of the catalyst. The methanol-based selectivity for dimethyl carbonate was 95% and the by-product methyl formate accounted for the remaining 5%.

Comparative Example 1

The procedure of Example 1 was repeated except that a gaseous mixture of CO/O$_2$/methanol=65/11/24 (by volume) was fed to the tubular reactor.

As a result, dimethyl carbonate was obtained at a rate of 1.0 mole/H per liter of the catalyst and the methanol-based selectivity for dimethyl carbonate was 83%.

Example 2

Using a reaction temperature of 140° C., an internal pressure of 20 Kg/cm$^2$ gauge and a feed gas of CO/O$_2$/methanol=92/1.5/6.5 (by volume), the reaction procedure of Example 1 was otherwise repeated.

As a result, dimethyl carbonate was obtained at a rate of 1.8 moles/H per liter of the catalyst and the methanol-based selectivity for dimethyl carbonate was 98%.

Example 3

Using a reaction temperature of 125° C., an internal pressure of 20 Kg/cm$^2$ gauge and a feed gas of CO/O$_2$/methanol=93/0.5/6.5 (by volume), the reaction procedure of Example 1 was otherwise repeated.

As a result, dimethyl carbonate was produced at a rate of 1.5 moles/H per liter of the catalyst and the methanol-based selectivity for dimethyl carbonate was 100%.

Example 4

The reaction procedure of Example 1 was repeated except that the packing thickness of the solid catalyst was set at 175 mm, the reaction temperature at 140° C., and the internal pressure of the tubular reactor at 20 Kg/cm$^2$ gauge and a feed gas of CO/O$_2$/methanol=92/1.5/6.5 (by volume) was introduced at a space velocity of 200 h$^{-1}$.

As a result, dimethyl carbonate was produced at a rate of 1.2 moles/H per liter of the catalyst and the methanol-based selectivity for dimethyl carbonate was 98%.

What is claimed is:

1. A method of producing a carbonic diester, having improved selectivity to said carbonic diester, comprising the step of:

contacting a reactor feed gas comprising oxygen, 1 to 20% by volume of an alcohol and 70 to 95% by volume of carbon monoxide with a solid catalyst containing copper which is effective for catalyzing oxidative carboxylation, wherein said catalyst is selected from the group consisting of a copper-containing inorganic compound, a copper alkoxy halide, a copper alkoxycarbonyl halide, a copper carboxylate, a salt of copper with a phenol, and a complex compound containing copper atom which is formed between an inorganic or organic copper compound and either an organophosphorus compound or a nitrile whereby said alcohol reacts with said carbon monoxide and said oxygen in a gas phase to produce said carbonic diester, wherein carbon monoxide and alcohol are present in the feed gas at a molar ratio (CO/alcohol) within the range of 3.5 to 95 and carbon monoxide and oxygen are present in the feed gas at a molar ratio (CO/O$_2$) within the range of 15 to 150.

2. The method of producing a carbonic diester according to claim 1, wherein said reactor feed gas comprises 4 to 18% by volume of said alcohol and 75 to 95% by volume of said carbon monoxide.

3. The method of producing a carbonic diester according to claim 1, wherein said solid catalyst containing copper atom is used in a supported form.

4. The method of producing a carbonic diester according to claim 1, wherein said alcohol is an alcohol comprising 1 to 6 carbon atoms.

5. The method of producing a carbonic diester according to claim 4, wherein said alcohol is methanol.

6. The method of producing a carbonic diester according to claim 1, wherein said alcohol is an alcohol having 1 to 6 carbon atoms, said solid catalyst contains copper atom, a carbon monoxide-alcohol molar ratio (CO/alcohol) of said feed gas is within the range of 3.5 to 95 and a carbon monoxide-oxygen molar ratio (CO/O$_2$) of said feed gas is within the range of 15 to 150.

7. The method of producing a carbonic diester according to claim 6, wherein said carbon monoxide-alcohol molar ratio (CO/alcohol) of said feed gas is within the range of 4 to 40 and said carbon monoxide-oxygen molar ratio (CO/O$_2$) of said feed gas is within the range of 20 to 100.

8. The method of producing a carbonic diester according to claim 6, wherein said alcohol is methanol and said solid catalyst containing copper atom is a copper halide.

9. A method of producing a carbonic diester according to claim 1, wherein the carbon monoxide to alcohol molar ratio (CO/alcohol) of said feed gas is within the range of 12 to 30 and the carbon monoxide-oxygen molar ratio (CO/O$_2$) of said feed gas is within the range of 20 to 100.

10. A method of producing a carbonic diester according to claim 1, wherein said solid catalyst is a copper-containing inorganic compound.

11. A method of producing a carbonic diester according to claim 10, wherein said copper-containing inorganic compound is a copper halide.

12. A method of producing a carbonic diester according to claim 11, wherein said copper halide is a cuprous halide.

13. A method of producing a carbonic diester according to claim 11, wherein said copper halide is cuprous chloride.

14. A method of producing a carbonic diester according to claim 1, wherein said solid catalyst is a complex compound containing copper and is formed between an inorganic or organic copper compound and triphenylphosphine.

15. A method of producing a carbonic diester according to claim 1, wherein said copper-containing inorganic compound is selected from a group consisting of copper nitrate, copper sulfate, copper carbonate, copper phosphate, copper carbonyl halide and copper borate.

16. A method of producing a carbonic diester according to claim 1, wherein said complex compound containing copper atom is formed between either cuprous chloride or copper acetate and either an organophosphorus compound or a nitrile.

17. A method of producing a carbonic diester, having improved selectivity to said carbonic diester, comprising the step of:

contacting a feed gas comprising oxygen, 4 to 18% by volume of an alcohol having 1 to 6 carbon atoms and 75 to 95% by volume of carbon monoxide with a solid catalyst comprising a copper halide supported on a solid support whereby said alcohol reacts with said carbon monoxide and said oxygen in a gas phase to produce said carbonic diester, wherein carbon monoxide and alcohol are present in the feed gas at a molar ratio (CO/alcohol) within the range of 4 to 40 and carbon monoxide and oxygen are present in the feed gas at a molar ratio (CO/$O_2$) within the range of 15 to 150 to enhance a selectivity for said carbonic diester.

18. A method of producing a carbonic diester according to claim 17, wherein said carbon monoxide and said alcohol are present in a molar ratio (CO/alcohol) in said feed gas within the range of 12 to 30 and carbon monoxide and oxygen are present in a molar ratio (CO/$O_2$) in said feed gas within the range of 20 to 100 to enhance a selectivity for said carbonic diester.

19. A method of producing a carbonic diester according to claim 17, wherein said feed gas further comprises an inert gas.

20. A method of producing a carbonic diester according to claim 17, wherein said alcohol is a monohydric alcohol.

21. A method of producing a carbonic diester according to claim 20, wherein said alcohol is selected from the group consisting of methanol and ethanol.

22. A method of producing a carbonic diester according to claim 17, wherein said copper halide is selected from the group consisting of cuprous halides and cupric halides.

23. A method of producing a carbonic diester according to claim 22, wherein said copper halide is selected from the group consisting of cuprous chloride and cupric chloride.

24. A method of producing a carbonic diester according to claim 17, wherein a proportion of said copper halide on said support is 0.1 to 50% by weight, based on the weight of said support.

* * * * *